United States Patent [19]

Anaya Fernandez de Lomana

[11] Patent Number: 5,505,701
[45] Date of Patent: Apr. 9, 1996

[54] INTRA-AORTIC BALLOON CATHETER

[76] Inventor: Eugenio F. Anaya Fernandez de Lomana, c/Princesa, 76 Madrid, Spain

[21] Appl. No.: 343,106

[22] Filed: Nov. 22, 1994

[30] Foreign Application Priority Data

Nov. 22, 1993 [ES] Spain ..................... 9302434

[51] Int. Cl.$^6$ ................................. A61M 29/00
[52] U.S. Cl. ........................ 604/99; 604/101; 604/102; 604/30; 604/66
[58] Field of Search ................. 604/96, 53, 19, 604/30, 66, 67, 65, 97, 98, 99, 101, 102, 113, 264, 280

[56] References Cited

U.S. PATENT DOCUMENTS

| | | | |
|---|---|---|---|
| 2,499,045 | 2/1950 | Walker et al. | 604/96 |
| 3,995,623 | 12/1976 | Blake et al. | |
| 4,705,502 | 11/1987 | Patel | 604/101 X |
| 4,705,507 | 11/1987 | Boyles | 604/101 |
| 4,950,226 | 8/1990 | Barron | 604/8 |
| 4,976,692 | 12/1990 | Atad | 604/101 |
| 5,059,178 | 10/1991 | Ya | 604/101 |
| 5,129,883 | 7/1992 | Black | 604/53 X |
| 5,135,474 | 8/1992 | Swan et al. | 604/8 |
| 5,256,141 | 10/1993 | Gencheff et al. | 604/101 X |
| 5,312,343 | 5/1994 | Krog et al. | 604/101 X |
| 5,320,604 | 6/1994 | Walker et al. | 604/96 |
| 5,328,470 | 7/1994 | Nabel et al. | 604/101 |
| 5,397,307 | 3/1995 | Goodin | 604/96 |

Primary Examiner—Corrine M. Maglione
Assistant Examiner—N. Kent Gring
Attorney, Agent, or Firm—Michael J. Striker

[57] ABSTRACT

An intra-aortic catheter apparatus for kidney perfusion and preservation has a catheter with a tube having an intermediate part which forms a permeable zone located so that in an inserted condition of the catheter the permeable zone is exactly located at a renal parahiliar area, a distal balloon located at a distal caudal part of the tube and formed so as to obstruct circulation in an aorta when being inflated, a proximal balloon located at an end of the tube which is insertable over renal arteries and having such a diameter that upon inflation it also fully obstructs aortic circulation, the balloons being located at opposite sides the of the permeable zone, a first opening provided in the tube and communicating with the permeable zone, a second opening provided in the tube so as to end in the renal parahiliar area, a distal opening communicating with the distal balloon for inflating the latter, and a proximal opening communicating with the proximal balloon for inflating the latter, and a monitoring equipment connected with the catheter.

2 Claims, 5 Drawing Sheets

INTRA-AORTIC BALLOON CATHETER

BACKGROUND OF THE INVENTION

The present invention relates to a double balloon catheter for intra-aortic insertion at the renal hilium, aimed at the diagnosis, prevention and treatment of acute kidney failure secondary to kidney hypoperfusion and, in case of death attributed to heart arrest, for "in situ" preservation of both kidneys to be later on used as renal grafts.

The insertion of the above catheter aims at a triple target, namely; a) instant and continuous recording of hemodynamic drifts and biochemical data at the renal hilium; b) maintenance of an optimal renal perfusion pressure (above or equal to 100 mmHg) as far and as long as there might be cardiac activity and direct administering at renal level of any substance whatsoever in the aim to prevent an acute kidney failure to be suffered by the patient, and c) "in situ" preservation of both kidneys to be later on used as renal grafts, in case of death attributed to heart arrest.

The balloon catheter for aortic contrapulsation is a standard therapeutical technique in the field of the mechanical circulatory assistance of the cardiogenic shock with the aim to maintain the left ventricular activity. Such a technique involves introduction of the catheter through the femoral artery up to the thoracic descending aorta. Through the use of an electrocardiogram (ECG) for due syncronization, the 30 to 40 cms baloon inflates during distole and deflates immediately after the left ventricular ejection. The purpose of the contrapulsation aims at increasing the coronary blood flow thus raising the diastolic perfision pressure (inflation of baloon) and further decreasing the oxygen requirements by the myocardium and improving the cardiac volume of flow thus reducing poscharge (balloon deflation). The hemodynamic effects of contrapulsation consist of: increase of the diastolic pressure with a raise of coronary flow; increase of the cardiac volume of flow (10–20%) and decrease of the left ventricular diastolic filling pressure. Contraindications involve disection or aneurysm of the thoracic or abdominal aorta.

Another baloon catheter for intra-aortic insertion has been aimed at the obtention of kidneys for further transplant, from cadaver donors dead from heart arrest. The first one to conceive this idea has been Wilson Se in 1968; however his catheter did not prove useful since it was provided with only one balloon and when perfusionning "in situ", perfusion fluid went to the limbs. The double balloon catheter was originally reported by Banowski Lh. et al although the clinical practice of the above technique was performed by Garcia-Rinaldi R. et al in 1975, who reported ten cases of functioning kidney transplants from cadaver donors dead from heart arrest.

In those countries where brain death (with beating heart) is admitted, organs for transplants are obtained from this type of cadavers; hence, the use of these catheters has been scarcely popular. It is however widely accepted in those countries where brain death is not admitted, such is the case of some European countries and Japan.

Undoubtedly, the report recently published in Clin. Transplantation (1993) by Itsuo Yokoyama et al, from the University of Nagoya (Japan) which shows the miximun experience which has ever been published on the use of the double balloon for the obtention of kidneys for transplants. It refers to 119 donors dead from heart arrest, wherein survival rate for receiver reaches 95.0% and 93.0% after 1 and 5 years respectively and the survival of the graft reaches 85.0% and 72.7% for the same 1 and 5 years respective terms. All of the above results are liable to be superposed to the best results attained from cadaver donors with beating heart.

In all cases, the insertion of the cathether is made through disection of the femoral aorta following heart arrest. Once the catheter has been inserted into the aorta, its placement is made by means of the pull-back technique, that is, by inflation of the balloons and further withdrawal, pulling down from the catheter thus fitting the lower balloon at the level of the aortic-ileac biffurcation. The mean time since the heart stops beating till the start of the kidney perfusion (hot ischemia time) used to be 12 minutes.

SUMMARY OF THE INVENTION

Accordingly, it is an object of the present invention to provide a intra-aortic catheter which is a further improvement of the existing catheters.

In keeping with these objects and with others which will become apparent hereinafter, one feature of the present invention resides, briefly stated, in an intra-aortic catheter which has a tube having an intermediate part which forms a permeable zone located so that in an inserted condition of the catheter the permeable zone is exactly located at a renal parahiliar area, a distal balloon located at a distal caudal part of the tube and formed so as to obstruct circulation in an aorta when being inflated, a proximal balloon located at an end of the tube which is insertable over renal arteries and having such a diameter that upon inflation it also fully obstructs aortic circulation, the balloons being located at opposite sides the of the permeable zone, a first opening provided in the tube and communicating with the permeable zone, a second opening provided in the tube so as to end in the renal parahiliar area, a distal opening communicating with the distal balloon for inflating the latter, and a proximal opening communicating with the proximal balloon for inflating the latter.

The catheter of the present invention is an intra-aortic catheter provided with two balloons to be percutaneously inserted through the femoral aorta into the abdominal aorta, at the renal area, either with synchronized or independent functioning between both balloons, with the purpose to maintain the proper kidney perfusion pressure with the aim to prevent an acute kidney failure in those patients affected by a low cardiac volume or flow attributed to cardiogenic shock. It is also further use to record the analytical drifts in other cases of renal hypoperfusion. The new cathether offers further important advantages.

It provides for the instantaneous and continuous recording of temperature, arterial pressure and blood flow at the renal parahilium, which may provide comprehensive information regarding renal physiology related to drifts of the renal circulation.

Direct blood extraction at the level of the kidney arteries may lead to the survey of the different substances which have influence over renal circulation under shock situations (renine, vasopresine, prostaglandines, etc.) (efferent tract).

Direct contact with the renal arterial circulation may also prove useful to administer any pharmacological substance, —either vessel-active or any other category whatsoever— which by altering intrarenal circulation might reveal some unknown facts which have so far been hidden under such circumstances (afferent tract).

By monitoring and maintaining renal perfusion pressure, a door is opened to the hope of recovery for those patients affected by cardiogenic shock, whose mortality rate is tremendously high.

Also, thanks to this catheter, a new source of kidney donors is attained.

Although this goal might even be broadened to preservation of further organs, such as liver or pancreas, it is at the moment aimed at the preservation of kidneys for further transplant to patients suffering from terminal kidney failure. The "in situ" preservation in this type of donors has already been demonstrated; however this new catheter provides the following advantages:

Percutaneous insertion of the same while the heart is beating and not under heart arrest.

Monitoring of the prerenal arterial circulation at the aortic level (hemodynamics, biochemimistry, etc.).

Renal pharmacological control to prevent acute kidney failure during the shock period.

Hot ischemia time (time elapsed since the heart stops beating till the start of the renal perfusion with the preservation fluid) is almost zero. This is extremely important since it is one of the main factors which influences over the immediate functionality or non-functionality of the renal graft.

Possibility to directly incorporate into the kidney any vessel active or immunosuppressive substance, together with the perfusion fluid (afferent tract).

Apart from the above preservation advantages, the main provision of this catheter lays upon its being a new source to get kidneys for transplants. To get an idea of the wide scope this present invention may cover, we must state and know that at present in Spain there are about 14,500 patients suffering from chronic kidney failure undergoing the dyalisis program, with an approximate cost of 60,000M Ptas/year. Out of the above patients, 6,000 of them are on the active waiting list and just some 1,300 patients/year are transplanted whereas others may not be transplanted due to scarcety of donors (it is however worthwhile mentioning that Spain is one of the European countries with the highest transplants/million inhabitants/year ratio).

Pretty hard to guess are the advantages such a source of donors may imply to those countries—such is the case of Japan—where there are at present more than 100,000 patients undergoing dyalisis, since transplants are hardly carried out since brain death donors are not admitted.

There is another point which must forgotten and that is that the use of this catheter may additionally imply a further series of significantly important economical advantages, as far as the following facts are considered:

The number of patients affected by hypoperfusion shock and liable to get the benefits from this catheter is approximately 10–15% higher than the total number of patients entering the Coronary Unit or the Intensive Care Unit. Upon the basis of the clinical characteristics of the same, their sanitary care is very expensive and the mortality rate is high. The use of this intra-aortic renal catheter may considerably lower the above referred extremely high costs since it may shorten the average stay time due to sooner recovery and avoidance of hemodyalisis or hemofiltering treatments for the prevention of acute kidney failure.

Its becoming a new source of donors for kidney transplants those from cadavers dead from heart arrest not only avoids the crossroad of the moral-cultural-legal problem related to brain death which is at present imposing so many difficulties on the donation of organs. Moreover it implies a giant's step on the economical field because each donor will imply savings worth 7 Million Pesetas for the society, since each patient undergoing dyalisis is worth an average 3,5M Ptas/year expense. The above by itself would justify that all of the hospitals which admit emergency patients with the support of intensive or coronary medicine reanimation services should be provided with the involved catheter.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
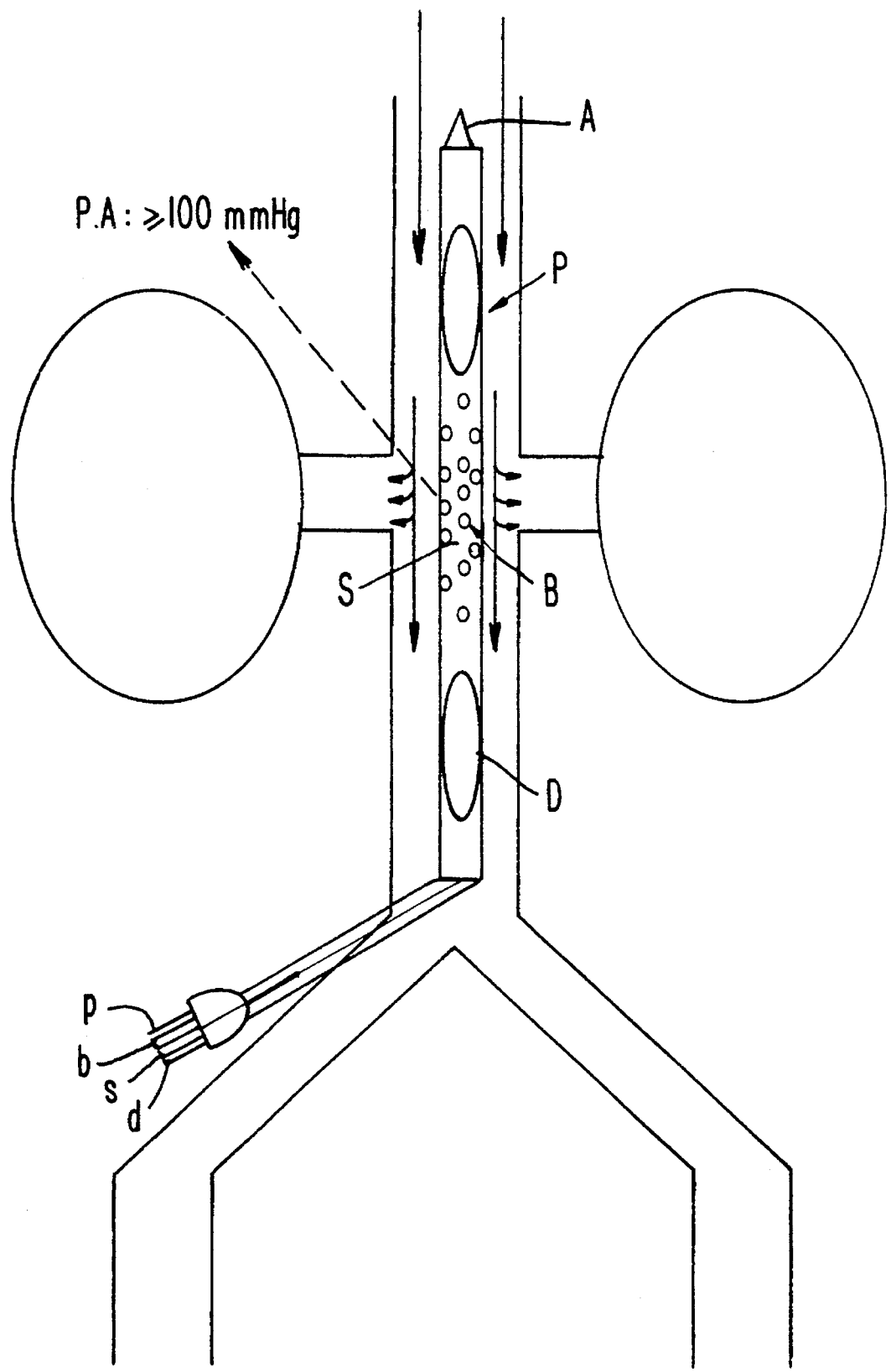
FIG. 1 shows a schematic view of the catheter inserted into the aorta, placed into operative position and ready to provide a full range of hemodynamic and biochemical information via efferent tract.

The catheter object of this present invention consists of a tube made of silicon or any other material whatsoever of those standarly used for intr-arterial catheters; it is 25–50 cms in length and 4 to 16 French in diameter. This catheter is provided with three of four lights, depending upon the technique, to be applied for its insertion, plus two baloons which inflate thus obstructing the artery at those points; it is further provided with an intermediary permeable zone.

A catheter in accordance with the present invention has a proximal balloon which is identified with reference numeral (P) and a distal balloon which is identified with reference numeral (D). A permeable zone (B) is located between the balloons. The catheter has a sensor channel (S). Furthermore, the catheter has an opening terminal (a) and an opening terminal (b) as well as a channel (d) and a channel (p).

Figure 2:
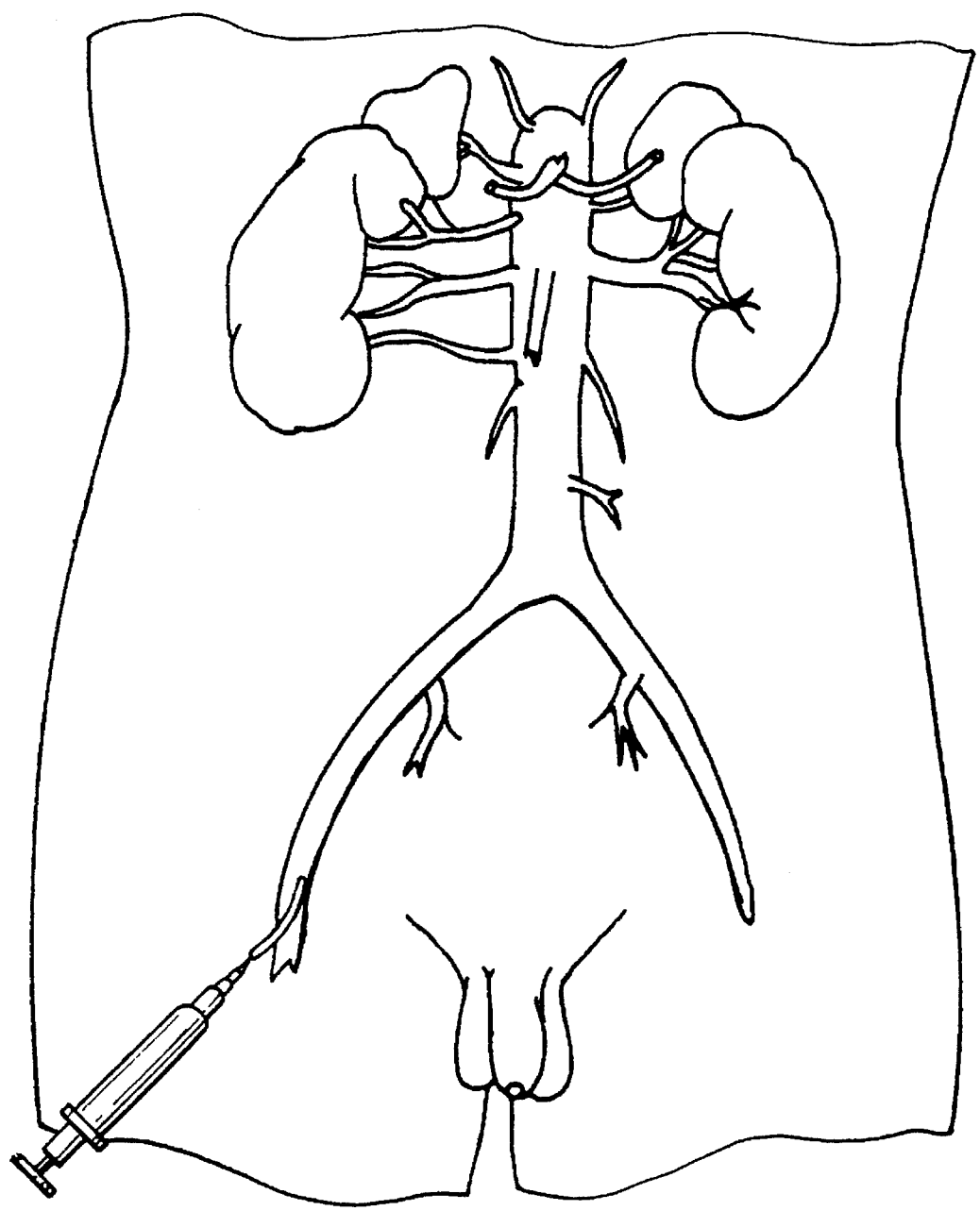
FIG. 2 shows the positioning and the way to insert the catheter object of this present description.
Figure 3:
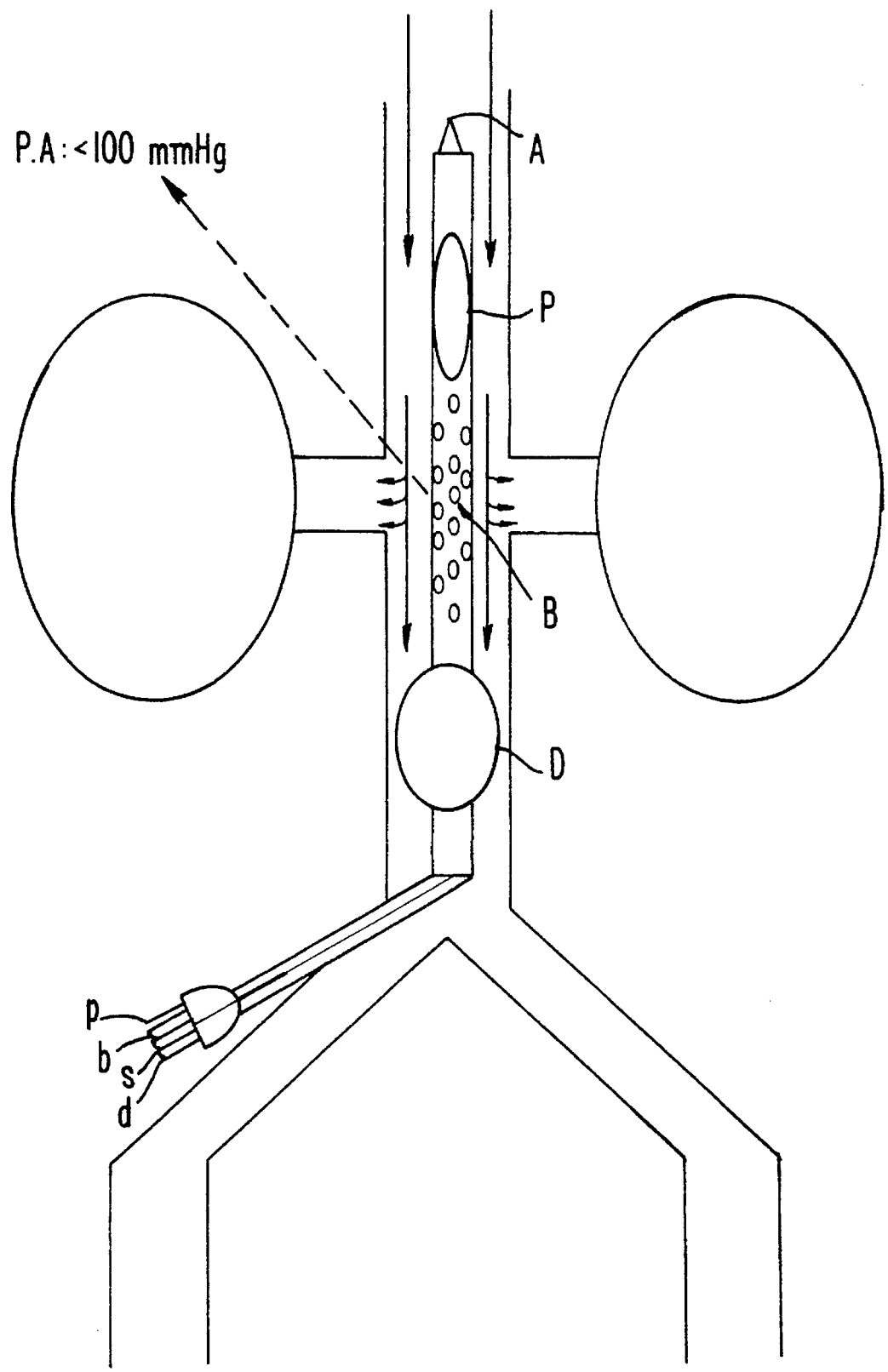
FIGS. 3 and 4 respectively shows the changes of the catheter when the arterial pressure in the area decreases and finally when the heart has irreversively stopped beating and an attempt is made to isolate and preserve the donor's kidneys.
Figure 4:
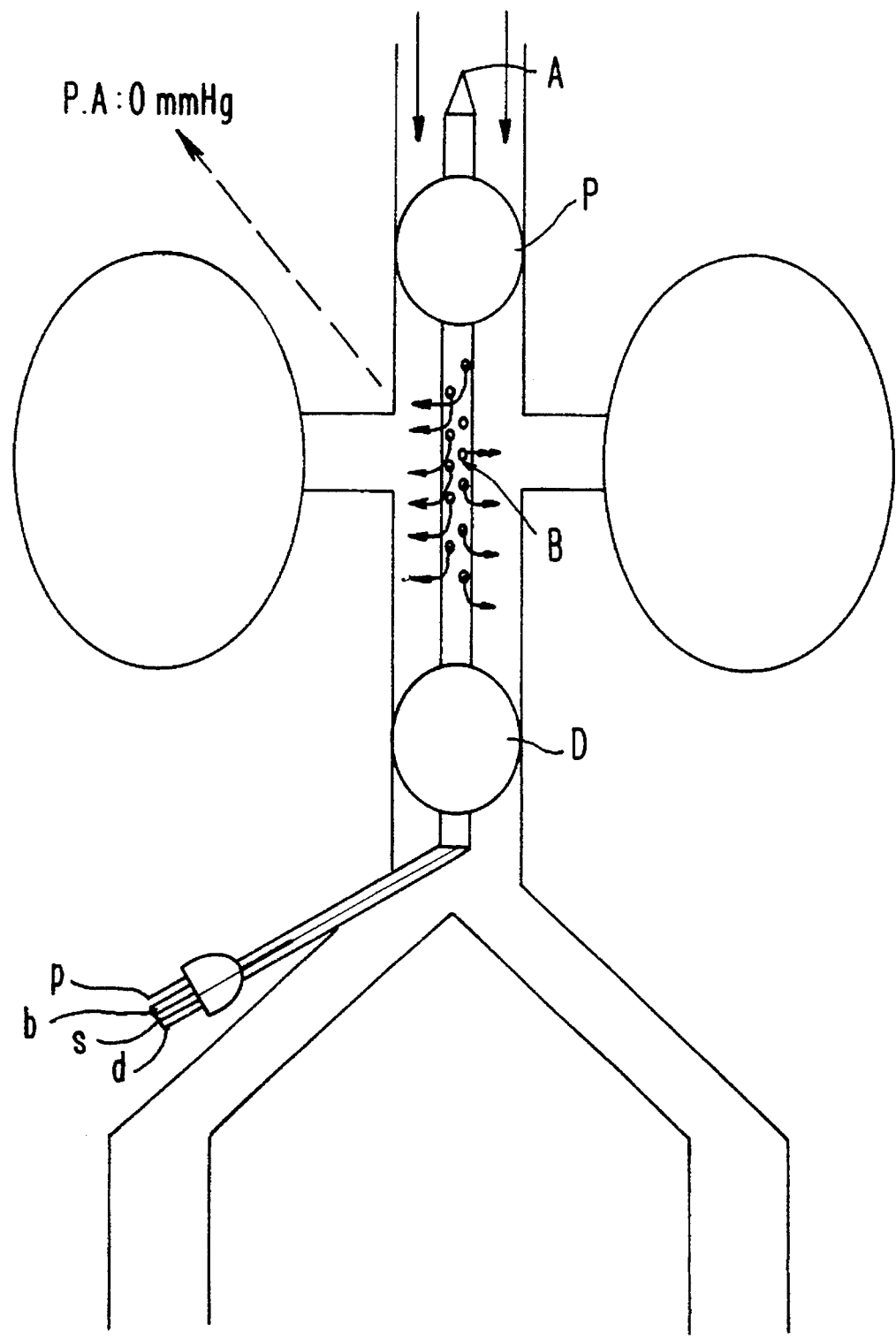

The catheter in accordance with the present invention is inserted into the aorta and placed into operative position as shown in FIGS. 1 and 2, and assumes the corresponding operational conditions as shown in FIGS. 3 and 4.

Figure 5:
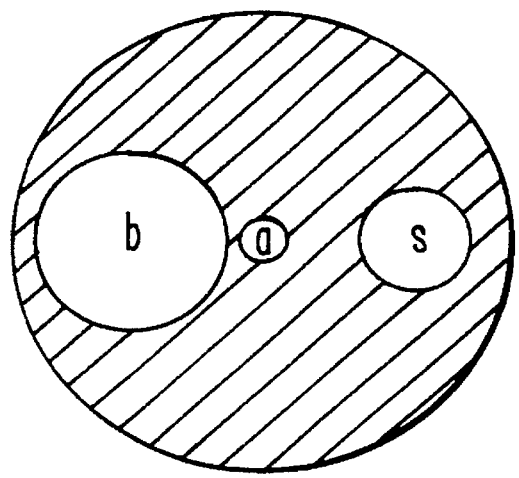
FIGS. 5, 6 and 7 show in a sectional view, three different types of catheters made according to this present invention.

In an embodiment shown in FIG. 5, the referred catheter is provided with the opening terminal. A guiding wire or "hair" according to the Seldinger's percutaneous technique is introduced through this opening. It may be disregarded whereas the insertion is made through a dilator-retainer attached to the catheter. The catheter further has the opening terminal (b).

It communicates with the permeable parahiliar-renal area (efferent and afferent tract). The sensor channel (S) communicates with the renal hilium area and its aim is the detection of blood temperature and pressure.

Such an embodiment is applied to those patients where a monitoring of all his/her renal vital constants is desirable for further taking eventual therapeutical decisions upon the basis of the attained information.

Figure 6:
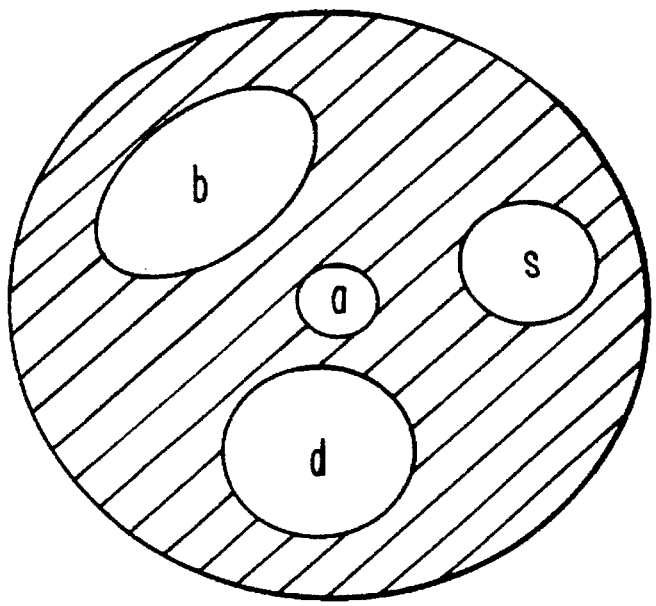

The embodiment shown in FIG. 6, apart from the above referred means includes the fourth (d) means which communicates with a distal baloon (D) to be placed under the renal arteries.

Figure 7:
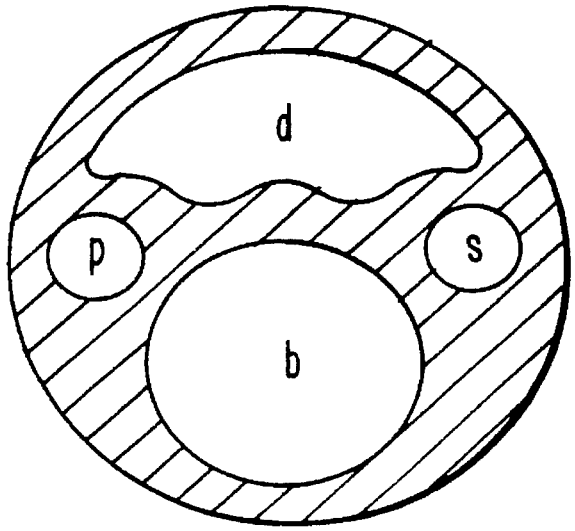

In the embodiment shown in FIG. 7, the light has been replaced to provide for the insertion of a metal guiding device for the insertion of the catheter (a) through a further channel (p) which communicates with a proximal balloon (P) placed over the renal arteries. Its function is, together with the distal baloon (D), to isolate to kidneys in the event of an irreversible heart arrest.

Obviously, further embodiments are possible. An alternative embodiment consists of a catheter provided with five channels which should include in addition to the above, the opening for the introduction of the insertion metal guiding device. A further alternative embodiment will include the sensors channel through the (b) channel which communicates with the permeable zone (B).

As it has already been stated, the catheter has the proximal balloon (P) located at the proximal end of the catheter, directly communicated with the opening (p) and it is going to be placed exactly above the renal arteries. It has such a diameter that completely obstructs the aortic circulation when inflated.

The distal balloon (D) is located on the distal or caudal side of the catheter. It is directly communicated with opening (d) and it is to be placed under the renal arteries. It is aimed at fulfilling a double commitment: in the event of a low cardiac volume of flow it will inflate and deflate either isolately or else through a contrapulsation mechanism with the purpose to maintain the proper renal perfusion, and in the event of an irreversible heart arrest it will inflate synchronically with the proximal balloon to completely obstruct the infrarenal aortic circulation.

The permeable zone (B) is a part of the catheter located between both balloons, exactly at the renal parahiliar area. It is permeable through the various holes and directly communicated with the opening (b). It has the objective to instantly control hemodynamic and biochemical drifts (efferent tract) at such a level and furthermore, to provide the means for the administration of any type of medical drug whatsoever directly into the renal circulation (afferent tract).

The catheter implantation can be made with the Selinger technique, characterizing the femoral artery. The catheter may be introduced either through the metal guiding device, through opening (a) as shown in FIGS. 5 and 6 or else, directly by means of a diameter dilator-retainer attached to the catheter such as shown in FIG. 7. Once it has been inserted, its placement shall be in such a position that the proximal balloon (P) and the distal balloon (D) will respectively be over and under the renal arteries. For due control, a contrasted radiological test or some other means must be applied to verify that renal circulation, including the anomalous polar arteries shall always stay between the two balloons (FIG. 1).

The different catheter terminals are connected to a monitor which will control and carry our the diverse functions the catheter has been developed for. Such a monitor will consist of several devices listed herebelow:

Electrocardiographer: This apparatus may be either incorporated to the monitor or else the monitor will have a connection output to a separate electrocardiographer which will be constantly monitoring the patient.

Hemodynamic and biochemical set. One of the deviations to terminal (s) has a series of sensors with output towards the renal parahiliar permeable zone which duly connected to the proper electronic transducers provide data on arterial temperature and pressure with the purpose to instantaneously and continuously monitoring arterial pressure at the renal parahiliar area.

Through channel (b), a little quantity of blood is extracted to instantaneously and continuously determine through an analizer the following analytical:

Gasometry (pH, pCO2, pO2, O2 saturation, basis excedent and bicarbonate, etc.)

A series of hematological parameters: hematocrit (Ht), hemoglobin (Hb), leucocite, platelet.

Biochemical parameter: glucose, creatinine in plasma (Crp), urea, iones (Na, K, Mg, Ca . . . ).

Non instantaneous determination of further substances such as enzymes (GOT, GPT, CPK, MB) vessel active molecules or pharmacological levels.

Ballons' inflation regulation set: both terminals (p) and (d) which respectively correspond to proximal balloon (P) and distal balloon (D) will indistinctly be connected to a pumping device which controls the regulates the inflation of the balloons. There are two different circumstances which set forth the inflation of the balloon, namely: a cardiogenic shock with low cardiac volume of flow or the event of irreversible heart arrest.

In the event of cardiogenic shock with an average renal parahiliar arterial pressure (ARAP) below approximately 80 mmHg registered on the permeable sone of the catheter the distal balloon starts inflation with the purpose to maintain ARAP within 100–130 mmHg (FIG. 3). The inflation mechanism of this balloon may occur either regularly or proportionally to the ARAP, or else, through a contrapulsation mechanism synchronized with the ECG, becoming inflated during diatole and deflated immediately before the left ventricular ejection. During the above clinical situation, the proximal balloon stays absolutely inactive;

In the event of heart arrest the inflation set is activated upon the following situation: plain ECG or ventricular fibrilation and AHAP equal to zero. Before being activated, and sound/visual alarm will be operative for 5 seconds. The activation mechanism will differ depending of the existence or inexistence of manual revival techniques (cardiac massage). In the first case, only the distal balloon will inflate proportionally to the AHAP with the massage. If the patient overcomes such a situation and his/her heart recovers its activity, the mechanism of the said balloon will continue functioning as if there had not been a heart arrest; however, in the course of the above heart arrest it will have provided a broad analytical information concerning all of the analytical and gasometric variables which will help to the future recovery of the patient. In the event of an irreversible heart arrest, the activation mechanism is much like the one on the phase of heart arrest without cardiac massage. There will also be an automatic manual device for safety reasons, before both balloons, the upper and the lower ones inflate to fully obstruct the aortic circulation over and below the renal circulation and the perfusion pumping set will synchronically start its functioning (FIG. 4).

Pumping set to administer all types of medical drugs or serums whatsoever while the patient is alive or, in the event of an irreversible heart arrest it will prove useful as perfusion to preserve the kidneys. The parahiliar permeable zone of the catheter is directly connected to a perfusion pump which is intended for a double purpose.

As far as there does not exist an inminent death risk, this is the idoneous channel for the administration of vesselactive substances, medical drugs or selective inmunodepressors;

Upon the death of the patient, it perfusses a renal perfusion fluid at above 0° C. to preserve the kidneys at an average 4° C. temperature. To attain a 0° C. perfusion of the above fluid which will have been formerly kept into a refrigerator at such a temperature, it will go through a cooling coil immersed into ice or else through a chamber provided with carbonic snow. A needle thermometer for percutaneous use and intrarenal registration of the temperature may optionally be used. The above thermometer may be either attached to the monitor or separately provided.

In the event of a perfusion pressure increase attributable to the volume of the administered fluid, an exanguination may be practised through one of the central venous catheters (yugular, subclavia or femoral), proportional to the renal perfusion pressure synchronizing the perfusion pump to a further exanguination pump which will take out a flow of blood equal to the flow of the perfuded fluid. Such an exanguination pump will be equipped with an hemoglobine sensor so that when the time comes the exanguinated fluid lacks such a substance, the circuit exclusively containing fluid for the renal perfusion will become closed. The volume of fluid to be perfuded for a good preservation of the kidneys from a biological point of view will be 2–3 liters. The rest of the perfuded fluid is just aimed at maintaining renal temperature at 4° C., being such a temperature which is related to the waiting time till the kidney is extracted and to the environmental conditions.

Once the renal extraction has been ended, the catheter will be pulled back and it is liable to be used again after due sterilization.

The above apparatus is also equipped with a computerized registering device where all of the hemodinamic, hematological and biochemical variables existing at every moment are recorded. Thus, the apparatus becomes a "black box" which keeps every and all circumstances which might have taken place in the patient while the catheter has been inserted into his/her body and connected to the apparatus. Such a function will be extremely important to know and analyze the different phenomena which occur during any surgical process or in the case of death. It may even provide important legal data to know and judge the work of the medical team in care of the patient.

It will be understood that each of the elements described above, or two or more together, may also find a useful application in other types of constructions differing from the types described above.

While the invention has been illustrated and described as embodied in a balloon catheter, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

I claim:

1. An intra-aortic catheter apparatus, comprising an intra-aortic catheter including an intra-aortic catheter for kidney perfusion and preservation, comprising a tube having an intermediate part with means forming a permeable zone located so that in an inserted condition of the catheter said permeable zone is exactly located at a renal parahiliar area, a distal balloon located at a distal caudal part of said tube and formed so as to obstruct circulation in an aorta when being inflated, a proximal balloon located at an end of said tube which is insertable over renal arteries and having such a diameter that upon inflation it also fully obstructs aortic circulation, said balloons being located at opposite sides said of said permeable zone, a first opening provided in said tube and communicating with said permeable zone, a second sensor opening provided in said tube and communicating with said permeable zone so as to end in the renal parahiliar area, a distal opening communicating with said distal balloon for inflating the latter, and a proximal opening communicating with said proximal balloon for inflating the latter; and an a monitoring equipment connected with said catheter and including an electrocardiographer, a plurality of sensors connected with said sensor opening and having an output toward said permeable zone connected with hemodynamic and biochemical set for providing data on arterial temperature and pressure so as to simultaneously and continuously monitor the arterial pressure at the renal parahiliar area; means for taking a blood sample through said first opening and determining gasometry, hematological and biochemical parameters and afterwards determining further biochemical and pharmacological data, a pumping device connected to said distal and proximal openings to control and carry out inflation of said balloons first activating the inflation of said distal balloon whenever a renal parahiliar pressure decrease or a reversible heart arrest is detected and activating the inflation of said proximal balloon in the event of an irreversible heart arrest, a perfusion pumping set connected with a terminal end of said permeable zone for perfusion of fluid through said permeable zone into kidney while a patient is alive and upon irreversible heart arrest an inflation of said balloons, providing an exanguination system connected with said catheter synchronized with said perfusion pumping set, and computerized registering means connected with said catheter and recording all hemodynamic, hematological and biological variables at every moment of operation of the catheter.

2. An intra-aortic catheter apparatus as defined in claim 1, wherein said tube further comprises an additional opening communicating with said permeable zone for inserting a guiding wire.

* * * * *